United States Patent
Deane et al.

(10) Patent No.: US 11,883,252 B2
(45) Date of Patent: Jan. 30, 2024

(54) SYSTEMS AND METHODS FOR MEASURING AN ORAL ARCH GEOMETRY AND SELECTING A MOUTHPIECE BASED ON ORAL ARCH MEASUREMENTS

(71) Applicant: KONINKLIJKE PHILIPS N.V., Eindhoven (NL)

(72) Inventors: Steven Charles Deane, Cambridge, MA (US); Vincent Jeanne, Migne Auxances (FR); Felipe Maia Masculo, Eindhoven (NL); Wilhelmus Johannes Everadus Evers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 772 days.

(21) Appl. No.: 16/982,615

(22) PCT Filed: Mar. 25, 2019

(86) PCT No.: PCT/EP2019/057351
§ 371 (c)(1),
(2) Date: Sep. 21, 2020

(87) PCT Pub. No.: WO2019/185497
PCT Pub. Date: Oct. 3, 2019

(65) Prior Publication Data
US 2021/0022840 A1  Jan. 28, 2021

Related U.S. Application Data

(60) Provisional application No. 62/649,234, filed on Mar. 28, 2018.

(51) Int. Cl.
A61C 19/04 (2006.01)
A61C 7/00 (2006.01)
(Continued)

(52) U.S. Cl.
CPC .............. *A61C 19/04* (2013.01); *A61B 5/067* (2013.01); *A61B 5/1076* (2013.01);
(Continued)

(58) Field of Classification Search
CPC ......... A61C 19/04; A61C 7/002; A61B 5/067; A61B 5/1076; A61B 5/1079; A61B 5/4542; A61B 5/4547; A61B 5/4552; A61B 5/682
See application file for complete search history.

(56) References Cited

U.S. PATENT DOCUMENTS

| 8,690,579 B2 | 4/2014 | Ikkink |
| 9,101,498 B2 | 5/2015 | Podmore |

(Continued)

FOREIGN PATENT DOCUMENTS

| CN | 204501067 U | 7/2015 |
| KR | 20180007659 A | 1/2018 |

(Continued)

OTHER PUBLICATIONS

International Search Report dated May 21, 2019.

*Primary Examiner* — Devin B Henson

(57) ABSTRACT

A system (10) and method for selecting a mouthpiece (25) for a user. The method includes receiving a signal with a personal care system (10) to initiate oral arch measurements using a personal care device (12). Data is collected from a position sensor (16) related to a location of a probe (14) of the personal care device as the probe is moved about an oral arch of the user. A controller (18) of the personal care system determines a dimension of the oral arch from the data. The controller selects a mouthpiece for the user based on the dimension of the oral arch. Information identifying the mouthpiece is transmitted to the user or other intended recipient.

15 Claims, 4 Drawing Sheets

(51) Int. Cl.
  *A61B 5/06*   (2006.01)
  *A61B 5/107*  (2006.01)
  *A61B 5/00*   (2006.01)
  *A61C 7/08*   (2006.01)
  *A61C 15/04*  (2006.01)
  *A61C 17/02*  (2006.01)
  *A61C 17/22*  (2006.01)

(52) U.S. Cl.
  CPC ............ *A61B 5/4542* (2013.01); *A61B 5/682* (2013.01); *A61C 7/002* (2013.01); *A61C 7/08* (2013.01); *A61C 15/046* (2013.01); *A61C 17/02* (2013.01); *A61C 17/221* (2013.01)

(56) References Cited

U.S. PATENT DOCUMENTS

| | | | |
|---|---|---|---|
| 9,326,594 B2 | 5/2016 | De Vries | |
| 10,064,711 B1* | 9/2018 | Richter | ................ A61C 17/221 |
| 2012/0037166 A1 | 2/2012 | Podmore | |
| 2013/0333133 A1 | 12/2013 | Miller | |
| 2015/0044629 A1 | 2/2015 | Wang | |
| 2016/0235357 A1* | 8/2016 | Ohmer | ................ A61B 5/6898 |
| 2016/0338803 A1* | 11/2016 | Pesach | ...................... G06T 7/74 |
| 2019/0231492 A1* | 8/2019 | Sabina | ............... A61C 13/0004 |

FOREIGN PATENT DOCUMENTS

| | | | | |
|---|---|---|---|---|
| WO | 2013173142 A1 | 11/2013 | | |
| WO | WO-2013173142 A1 * | 11/2013 | ........... | A61B 5/0088 |
| WO | 2016180929 A1 | 11/2016 | | |
| WO | 2017068453 A1 | 4/2017 | | |
| WO | 2017102859 A1 | 6/2017 | | |

* cited by examiner

US 11,883,252 B2

SYSTEMS AND METHODS FOR MEASURING AN ORAL ARCH GEOMETRY AND SELECTING A MOUTHPIECE BASED ON ORAL ARCH MEASUREMENTS

This application is the U.S. National Phase application under 35 U.S.C. § 371 of International Application No. PCT/EP2019/057351, filed on Mar. 25, 2019, which claims the benefit of U.S. Provisional Application Ser. No. 62/649,234, filed Mar. 28, 2018. These applications are hereby incorporated by reference herein.

FIELD OF THE INVENTION

The present disclosure is directed generally to personal care systems and methods, and more particularly to systems and methods for measuring oral arch geometries and selecting a mouthpiece corresponding to measured oral arch geometries.

BACKGROUND

Mouthpieces are used in the dental industry for a variety of purposes, such as whitening, applying particular dental chemistries for extended periods to the teeth or gingiva to improve oral hygiene, brushing all teeth at the same time, or other uses. Commercial sale of a "one size fits all" mouthpiece is impractical due to the large variety of oral geometries that exist. For example the oral arch length in adult mouths can vary by approximately a factor of two. Additionally, the shape of the oral arch can be generally rounded, square, or 'V' shaped, with variations amongst each shape. The manufacture of a well-fitting mouthpiece requires measurement of each individual's unique oral arch geometry, typically requiring expensive equipment or assistance by a dental professional. As a result, many users either have a custom fit mouthpiece made, which is often inconvenient and expensive, or use a poorly fit mouthpiece, which has compromised functionality.

Accordingly, there is a continued need in the art for systems and methods that enable users to more readily obtain mouthpieces tailored to their specific oral arch geometries.

SUMMARY OF THE INVENTION

The present disclosure is directed to inventive systems and methods for measuring a user's oral arch geometry and selecting a mouthpiece corresponding to the measured geometry. Various embodiments and implementations herein are directed to a system having a personal care device configured with a position sensor arranged to collect data representative of a position of a probe of the personal care device. The system determines one or more oral arch measurements of the user based on the collected data as the probe is moved about the user's mouth. The system may be arranged to instruct the user to follow a specific pattern. A mouthpiece is selected for the user based on the particular oral arch geometry measured to ensure that the mouthpiece accurately fits the user.

Generally, in one aspect a method for selecting a mouthpiece for a user is provided. The method includes receiving a signal with an personal care system to initiate oral arch measurements using a personal care device; collecting data from a position sensor related to a location of a probe of the personal care device as the probe is moved about an oral arch of the user; determining, by a controller of the personal care system, a dimension of the oral arch from the data; selecting, by the controller, a design for a mouthpiece for the user based on the dimension of the oral arch; and transmitting information identifying the mouthpiece to an intended recipient.

According to an embodiment, the method further comprises transmitting a sequence of a plurality of oral arch positions at which the user is instructed to touch the probe of the personal care device. According to an embodiment, the positions in the sequence include at rear molars, at front teeth, at canines, or a combination including at least one of the foregoing. According to an embodiment, at least a portion of the sequence is repeated or reversed in order and then repeated.

According to an embodiment, the determining includes: obtaining a velocity of the probe from the data; generating a velocity curve as the velocity over time; identifying a plurality of local minimums in the velocity curve; integrating an area under the velocity curve and between an adjacent pair of local minimums; and determining the dimension of the oral arch as a result of the integrating.

According to an embodiment, the method further includes correlating each of the positons to one of the local minimums using a known order of the sequence. According to an embodiment, the method further includes connecting a line between the adjacent pair of local minimums, and bounding the area with the line to eliminate drift or sensor error during the integrating. According to an embodiment, the data includes acceleration data and the obtaining includes integrating the acceleration data.

According to an embodiment, the position sensor includes a plurality of position sensors and the collecting includes collecting data with each of the positions sensors. According to an embodiment, the plurality of position sensors includes a camera or proximity sensor and an inertial measurement unit.

According to an embodiment, the controller is included by the personal care device, a remote device separate from the personal care device, or a combination including at least one of the foregoing. According to an embodiment, the remote device is a charging station, smartphone, or other computing device in communication with the position sensor.

Generally, in another aspect, a personal care system is provided. The personal care system includes a personal care device having a probe; a position sensor configured to collect data related a position of the probe; and a controller configured to: determine a dimension of an oral arch of a user from the data; select a design for a mouthpiece for the user based on the dimension of the oral arch; and transmit information identifying the mouthpiece to an intended recipient.

According to an embodiment, the personal care device is an electric toothbrush, an interdental cleaning device, a flossing device, or an oral irrigator. According to an embodiment, the personal care system further includes a remote device in communication with the position sensor, the remote device comprising the controller.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of systems and methods for measuring a user's oral arch geometry and selecting a mouthpiece based on the oral arch measurements. A particular goal of utilization of certain embodiments of the present disclosure is to enable users to select a well-fitting mouthpiece without the need for the user to visit a dental professional.

In view of the foregoing, various embodiments and implementations are directed to a system having a personal care device configured with a position sensor arranged to collect data representative of a position of a probe of the personal care device. The system determines one or more oral arch measurements of the user based on the collected data as the probe is moved about the user's mouth. The system may be arranged to instruct the user to follow a specific pattern. A mouthpiece is selected for the user based on the particular oral arch geometry measured to ensure that the mouthpiece accurately fits the user.

Figure 1:
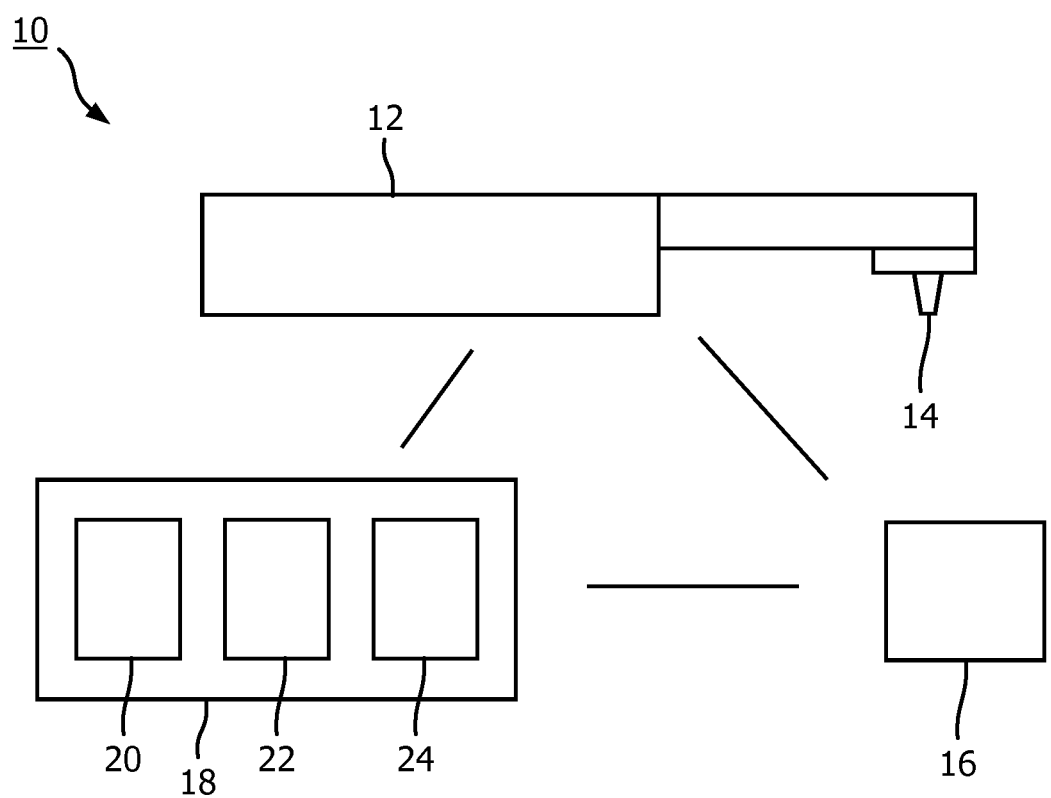
FIG. 1 schematically illustrates a personal care system for measuring a user's oral arch geometry and selecting a design for a mouthpiece for the user according to one embodiment disclosed herein.

Referring to FIG. 1, a personal care system 10 is provided that includes a personal care device 12 having a probe 14 arranged to be inserted into the user's mouth or otherwise put into contact with, or in proximity to, a user's teeth. The personal care system 10 also includes a position sensor 16 (or position sensors 16) configured to determine a position of the device 12, or a component of the device 12 such as the probe 14, relative to a user's mouth or teeth. The personal care device 12 may include an electric toothbrush, a flossing device, an interdental cleaning device, an oral irrigator, or any other type of personal care device, such as an electric shaver. The probe 14 may be a conventional bristled toothbrush head or other arrangement. In one embodiment, such as shown in FIG. 1, the probe 14 is a truncated conical and/or contoured probe (such as used in many flossing or interdental cleaning devices). A contoured or truncated conical probe may be advantageous because it is less flexible than toothbrush bristles, thereby enabling the probe 14 to be more precisely located in particular locations within the user's mouth. For example, accurate location measurements by the position sensor 16 can be achieved by firmly pressing a contoured or conical probe into interdental spaces or grooves between the teeth. In this way, positioning the probe 14 in the user's mouth can be more easily and consistently achieved by the user, thereby leading to more precise measurements by the position sensor 16.

More generally, it is to be appreciated that an oral care device such as an electric toothbrush or interdental cleaning device is one example of a personal care device 12 that can be used with the system 10 for measuring the dimensions of a user's oral arch as discussed herein. In other embodiments, the personal care device 12 may be an electric shaver, facial cleaning device, etc., which has the sensor 16 embedded therein. Accordingly, it is also to be appreciated that the probe 14 is one example of a probe for the personal care device which is intended to be pressed against the user's facial or oral features to ensure a more accurate reading. While the probe of a protrusion, such as the probe 14, works well for such a purpose, the probe could be any other structure of a personal care device. Additionally, any such probe can be contacted against a user's cheek instead of directly against their teeth. For example, an electric shaver equipped with the sensor 16 may be traced along a user's cheek about the oral arch. In one embodiment, a smartphone or other position sensor-enabled device may be used to perform the measurements.

A controller 18 is also included in the system 10 and has a processor 20, a memory 22, and/or a communication module 24 to facilitate and/or monitor operation of the device 12, the sensor 16, or other components of the system 10. In one embodiment, the controller 18 is embedded in the device 12, while in other embodiments the controller 18 may be included in a remote device 26, such as a docking or charging station for the device 12, a smartphone or other computing device in communication with the device 12 (e.g., via the communication module 24), a server or cloud-implemented computing infrastructure, etc.

The processor 20 may take any suitable form, such as a microcontroller, plural microcontrollers, circuitry, a single processor, or plural processors configured to execute software instructions. The memory 22 may take any suitable form or forms, including a volatile memory, such as random access memory (RAM), or non-volatile memory such as read only memory (ROM), flash memory, a hard disk drive (HDD), a solid state drive (SSD), or other data storage media. The memory 22 may be used by the processor 20 for the temporary storage of data during its operation. Data and software, such as the algorithms or software necessary to analyze the data collected by the position sensor 16, an operating system, firmware, or other application, may be installed in the memory 22. The communication module 24 is arranged to enable wired or wireless signal communication between the position sensor 16 and controller 18. The communication module 24 may be or include any module, device, or means capable of transmitting a wired or wireless signal, such as but not limited to Wi-Fi (e.g., IEEE 802.11), Bluetooth, cellular, optical, magnetic, Ethernet, fiber optic, or other technologies.

Figure 2:
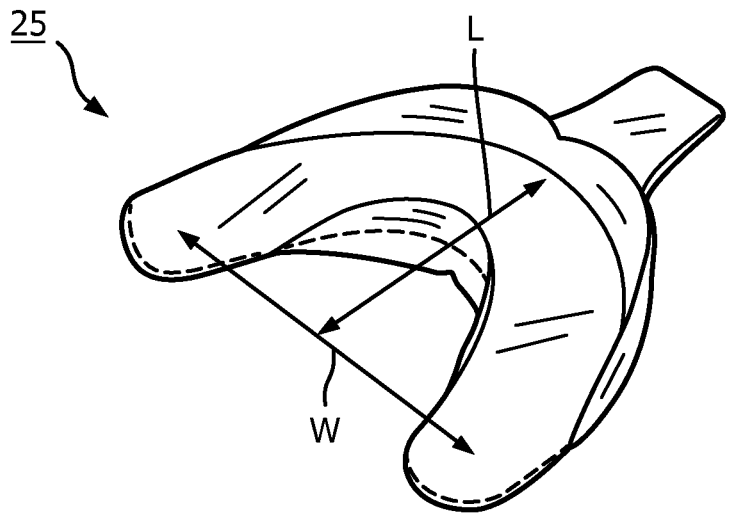
FIG. 2 illustrates a mouthpiece having at least one width dimension and at least one length dimension.

The position sensor 16 may include any device configured to determine the position of the device 12, notably the probe 14, with respect to the user's teeth. As discussed in more detail below, by monitoring the position of the probe 14, the various dimensions of the user's oral arch can be determined by analysis of data collected by the position sensor 16. Based on the user's unique oral arch dimensions or measurements, the system 10 is arranged to identify a correspondingly sized mouthpiece. For example, FIG. 2 illustrates a mouthpiece 25 according to one embodiment, which includes at least a width W and a length L. As discussed in more detail below, widths and lengths at various points in the user's oral arch can be determined by the personal care system 10 to identify and/or select a mouthpiece design that is customized to the user's unique oral arch geometry. It should be appreciated that the mouthpiece 25 is provided as one representative example, but that mouthpieces of various shapes, sizes, and/or features may be included. For example, the mouthpiece 25 may include individual compartments for each tooth, include larger or smaller side walls, etc. It is also to be appreciated that the term "mouthpiece" as used herein includes any mouth guard or oral care tray (e.g., for whitening or applying other dental substances to the user's teeth) that at least partially envelopes or contacts a user's teeth.

It is to be appreciated that the position sensor 16 can include any relevant position sensing technology, e.g., embedded ultrasonic, infrared, or other proximity sensors, accelerometers, gyroscopes, magnetometers, etc. It is also noted that the sensor 16 may be externally located with respect to the personal care device 12, such as a camera of a remote device 26, e.g., a smartphone, "smart minor", or other computing device in communication with the personal care device 12. In one embodiment, the controller 18 and/or the position sensor 16 comprise or are comprised by such a remote device 26 (or both the device 12 and such a remote device include the controller 18 and the sensor 16). In this way, remote devices can be in communication with the device 12 via a communication module such as the module 24, either directly or indirectly via another device (e.g., both the device 12 and the remote device 26 are connected to the internet and communicate via cloud infrastructure).

The system 10 may also contain multiple instances of the position sensor 16 (e.g., both an external camera and an embedded position sensor), and the data from each of the sensors 16 may be combined or fused (e.g., via the controller 18) to further improve accuracy. For example the device 12 containing an IMU or other embedded sensor may be supplemented by a smartphone camera to detect user head motion, with the controller 18 arranged to correct for the detected head movement, or to prompt the user to keep their head still during brushing. As another example, the position sensor(s) 16 may include both an IMU and a proximity sensor embedded in the device 12 to provide a self-contained device in which the proximity sensors provide a device-user measurement (e.g., position of the user's head, mouth, or teeth with respect to the probe 14) to account for movement of the user's head and improve the position data collected by the IMU.

Figure 3:
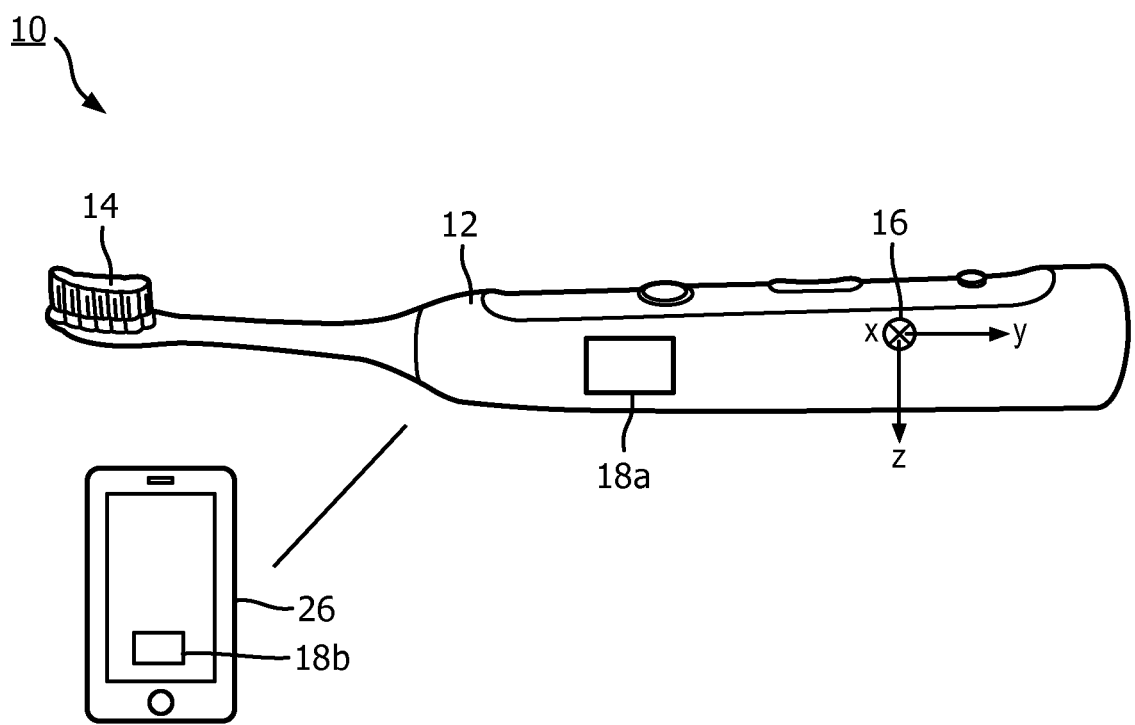
FIG. 3 illustrates one specific embodiment for the general system of FIG. 1 in which an electric toothbrush is arranged with an embedded inertial measurement unit and in communication with a smartphone.

One particular embodiment is illustrated in FIG. 3, in which a personal care system 10 is shown having a personal care device that is an electric toothbrush 12. The electric toothbrush 12 has a probe 14 formed as or in a brush head, and a position sensor formed as an embedded inertial measurement unit (IMU) 16 for measuring its position with respect to x, y, and z coordinates, as shown. It is to be appreciated that the components of FIG. 3 include several reference numerals that are used in the other Figures but appended with alphabetic ('a', 'b') suffixes to facilitate discussion of the specific features of the system 10. Any disclosure made herein with respect to a component having the same base reference numeral is generally applicable to the versions of that component appended with a suffix (e.g., the description of the controller 18*a*, 18*b* is generally applicable to the system 18, etc.).

The toothbrush 12 is in communication with a remote device 26 in the form of a smartphone or mobile device, e.g., via controllers 18*a* and 18*b* of the toothbrush 12 and the remote device 26. The smartphone 26 may include a software application configured to enable a user to interface with the toothbrush 12 and/or for the toothbrush 12 to communicate information to the user. It is to be appreciated that FIG. 3 is provided as one non-limiting example to aid in the appreciation of the embodiments envisioned and disclosed herein. For example, the electric toothbrush 12 may include the IMU 16' to collect data that enables the electric toothbrush 12 to provide coaching functionality in which the toothbrush 12 monitors and assesses a user's brushing habits so that it can offer analysis to improve the user's brushing technique (e.g., via a software application installed on the smartphone 26). An example of such an electric toothbrush is made commercially available by Koninklijke Philips N.V. and marketed under the name DiamondClean Smart.

To ensure that the data collected by the position sensor 16 is able to be accurately used by the controller 18 to calculate oral arch measurements, the user can be instructed to move the probe 14 in an instructed pattern or sequence between a series of specific locations in the user's mouth. In one embodiment, the instructions are provided via a remote device 26, such as a smartphone, via printed instructions, via a display or sound prompts from the device 12 (e.g., a video or animation), etc. The instruction could be pre-recorded, or updated in real time as the data from the position sensor 16 is analyzed by the controller 18 to identify that the probe 14 has reached each instructed position, e.g., by identifying pauses in the movement as discussed in more detail below. By way of specific example, in one embodiment, the user may be instructed to move the probe 14 from the rear molars at one side of their mouth to their front teeth and then to the rear molars on the other side of their mouth. Those of ordinary skill in the art will recognize other sequences that can be utilized. The user may be instructed to repeat the sequence any number of times, e.g., by repeating the sequence or reversing the sequence.

The movement sequence can for example be an instruction to touch the probe 14 (e.g., toothbrush bristles, contoured probe, etc.) to different positions within the user's mouth, e.g., the outside of the rear molars, against the front teeth, at the canines, etc. For example, the user in some embodiments may be instructed alternate between sides, to touch specified points in succession around the perimeter of the user's oral arch, or to touch the probe 14 against random points around the user's oral arch. The pattern, or any portion of the pattern, can be repeated and/or reversed, any number of times. The upper and lower arches can be measured separately or a single measurement can be used to approximate both. In one embodiment, the offset between the upper and lower arches (overbite or underbite) is measured to approximate the dimensions of one oral arch based on the measurements taken with respect to the other.

The sequence can be a regular sequence (e.g. left molar outer—front outer—right molar outer—front outer—left molar outer) which can be repeated a number of times. Alternately, it can be a random or pseudo-random sequence, e.g., generated by the controller 18 using a random number generator or the like, which may provide more robust separation from drift and residual user motion. For example a random or pseudo-random sequence will avoid potential errors due to regular user motion, but may be more difficult for the user to follow. In one embodiment, a remote device 26 such as the smartphone is used to "gamify" the instructed sequence by providing audiovisual prompts, assigning or displaying a score, points, or a user's progress toward an accurate set of measurements based on the user's actions, etc.

To most accurately measure the oral geometry, the movement between the instructed locations can be made separateable from the drift in the position sensor 16, which is typically slowly changing over time. That is, when measuring absolute position, some position sensors, such as IMUs, may be prone to errors that accumulate over time (e.g., due to drift, having to measure accelerations with a large offset due to gravity, etc.). In one embodiment, drift is accounted for by ensuring that the instructed sequence requires the user to pause intermittently or change direction of motion significantly and repeatedly over short periods of time. This is readily achieved by making a sequence, for example repeated back and forth steps between sites, over short periods of time, e.g. a few seconds. For example, a user may be instructed to place the probe 14 at the rear molars on one side, at the front teeth, at the rear molars on the other side, and back again. Additionally, if the absolute position of the probe 14 is being measured by the position sensor 16, then movement of a user's head will change the relative positioning of the position sensor 16 with respect to the user's teeth, but will not be reflected in the data collected by this type of position sensor. As discussed above, the use of external sensors, such as cameras, or proximity sensors can be useful to identify and/or correct for movement of the user's head relative to the device 12.

Figure 4:
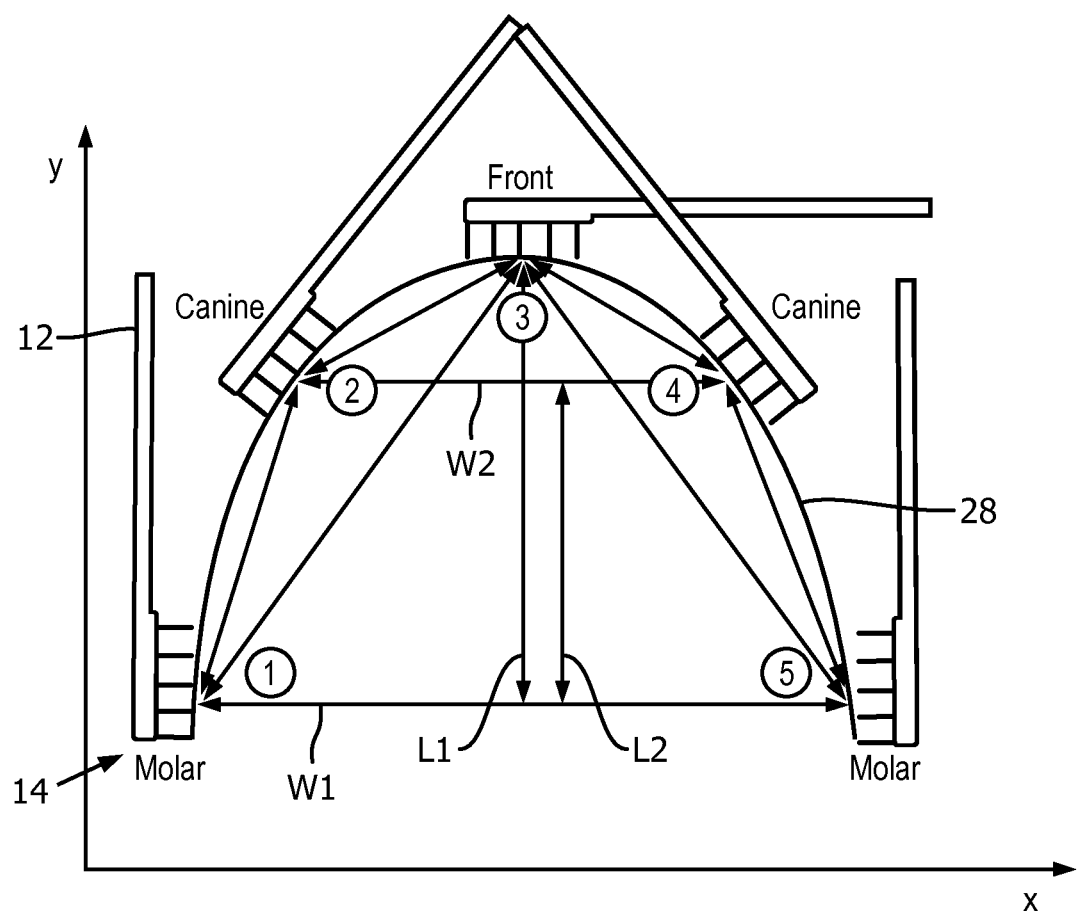
FIG. 4 schematically illustrates a probe of a personal care device at various positions of a user's oral arch for determining the geometry of the oral arch according to one embodiment disclosed herein.

Examples of instructed sequences can be appreciated in view of FIG. 4, which illustrates the probe 14 of the device 12 being positioned at different locations relative to a representative oral arch 28. The positions in FIG. 4 are indicated by the encircled numbers 1 through 5. In the illustrated example, five oral cavity position locations are indicated: two at the rear molars (positions 1 and 5), one at the front teeth (position 3), and two at the canines (positions 2 and 4). It is to be appreciated that fewer positions could be used in other embodiments. For example, in one embodiment the measurement positions include just the two molars and the one at front teeth (positions 1, 3, and 5), which would be sufficient to determine at least a length of the oral arch (i.e., a first oral arch length L1) as well as a width of the oral arch (i.e., a first oral arch width W1). By including the positions at the canines (the positions 2 and 4), additional lengths and widths can be determined, such as a second width W2 of the oral arch at the canines and a second length L2 from the molars to the canines. Similarly, a greater number of positions could be used, e.g., including the incisors, front molars, or even a measurement position at each tooth and/or at the interdental space between each adjacent pair of teeth. Using more locations may be beneficial in some embodiments to achieve a more accurate measurement of the oral arch 28, e.g., in order to differentiate between 'U' and 'V' shaped jaws by including the canines in addition to the molars and front teeth. From these lengths and widths, the mouthpiece can be selected to accurately fit the user's unique oral arch geometry. Additional measurement positions may be advantageous for more rigid mouthpieces and/or mouthpieces for procedures that require smaller tolerances.

The position data collected by the position sensor 16 can be used to determine the position of the probe 14 according to any applicable function, algorithm, or technology. For example, if an embedded IMU or similar position sensor is used, then the velocity of movement of the sensor as well as the pointing direction of the probe 14 can be determined, and the geometry of the oral arch can be calculated from this data. For example, the velocity of the device can be calculated by integration of the accelerometer output after compensation of the gravitational acceleration component.

Figure 5:
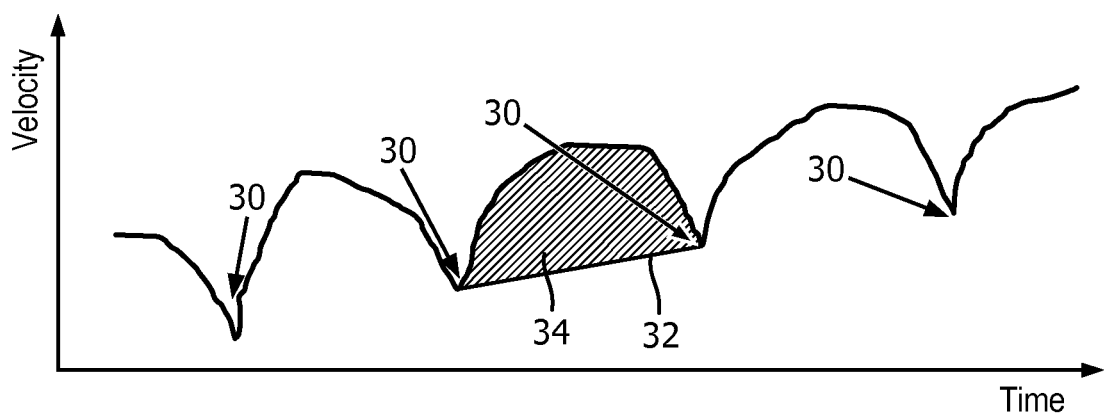
FIG. 5 illustrates a graph plotting velocity data with respect to time that can be used to determine a user's oral arch geometry according to one embodiment disclosed herein.

FIG. 5 shows a graph plotting the calculated velocity data with respect to time as a user follows a sequence to touch different oral arch positions in an instructed pattern. The velocity of the probe 14 can be analyzed by the controller 18 for the points at which the user pauses briefly or changes direction when the probe 14 reaches each instructed location. While the velocity is not expected to read exactly zero at the locations indicated by pauses (e.g., due to residual head motion of the user, drift in the position sensor 16, or other source of error), each oral arch position in the instructed sequence can be determined by identifying local minima 30 in the data. That is, each local minimum 30 represents a position at which the user briefly paused movement of the probe 14, such when coming into contact with their teeth at the indicated location, or to change direction to move the probe 14 to the subsequent location. Since the order of locations is known (as defined by the instructed sequence), the data corresponding to each of the positions can be correlated to the proper positions by identifying the local minima 30 in turn. It is also noted that the data, such as the velocity data shown in FIG. 5, is expected to follow a regular pattern that has data that is within expected value ranges as the user moves the probe between each position. The system 10 can accordingly be configured to perform a consistency check such that if the motion data does not correspond to these expected ranges, that portion of the data can be flagged or deleted. In one embodiment, the system 10 is arranged to instruct the user to repeat the sequence or a portion of the sequence, corresponding to flagged data.

Distance between two of the identified sequence positions can be determined from the velocity data by integrating the area under the velocity curve. Furthermore, in one embodiment a line, e.g., a line 32 may be drawn connecting adjacent pairs of the local minima 30 in order to reduce drift or error. That is, by drawing the line 32, and integrating the velocity/time data above this baseline indicated by a hatched area 34, the physical distance between the located site of each pause (as identified by the local minima 30) is more accurately estimated for each step between the instructed oral arch positions. If an IMU or similar sensor is used for the sensor 16, the distance can be measured in three dimensions, and the pointing direction of the probe 14 can also be estimated. The pointing direction can aid the determination of oral arch size, such by assisting in the estimation of the curvature of the arch (e.g., different angles at the canines corresponding to more 'V' or 'U' shaped oral arches).

If the personal care device 12 is a powered device, such as an electric toothbrush, optionally the motor can be disabled during the measurement. This can be useful to enhance the comfort and ease for the user when repeatedly locating the probe 14, and also may improve accuracy of the readings made by the position sensor 16, as any effects from vibrations of a motor are eliminated. This may be achieved by the user manually manipulating a setting on the device 12, or interfacing with the device 12 via a software application on a remote device 26. If the probe 14 is a specifically designated component configured to strictly perform oral arch measurements, the device 12 may be configured to automatically detect and/or recognize the probe 14 by use of a radiofrequency identification (RFID) chip or similar identification technology. For example, the aforementioned DiamondClean Smart toothbrush is configured to detect different mechanisms that are removably attachable to the base of the toothbrush.

For increased accuracy, the motion sequence can be designed in such a way that the direction of the translational movement of the probe 14 is simplified in the coordinate system used by the position sensor 16. For example, with respect to the toothbrush 12 and the x, y, z coordinate system of FIG. 3, the user could be asked to perform the motion sequence with the bristles of the brush head 14 pointed upward as the side of the brush head 14 is touched to the user's teeth at each location. In this case, no translational motion would be expected in the z-direction of the coordinate system, thus simplifying the analysis to two dimensions (x and y in this case).

Figure 6:
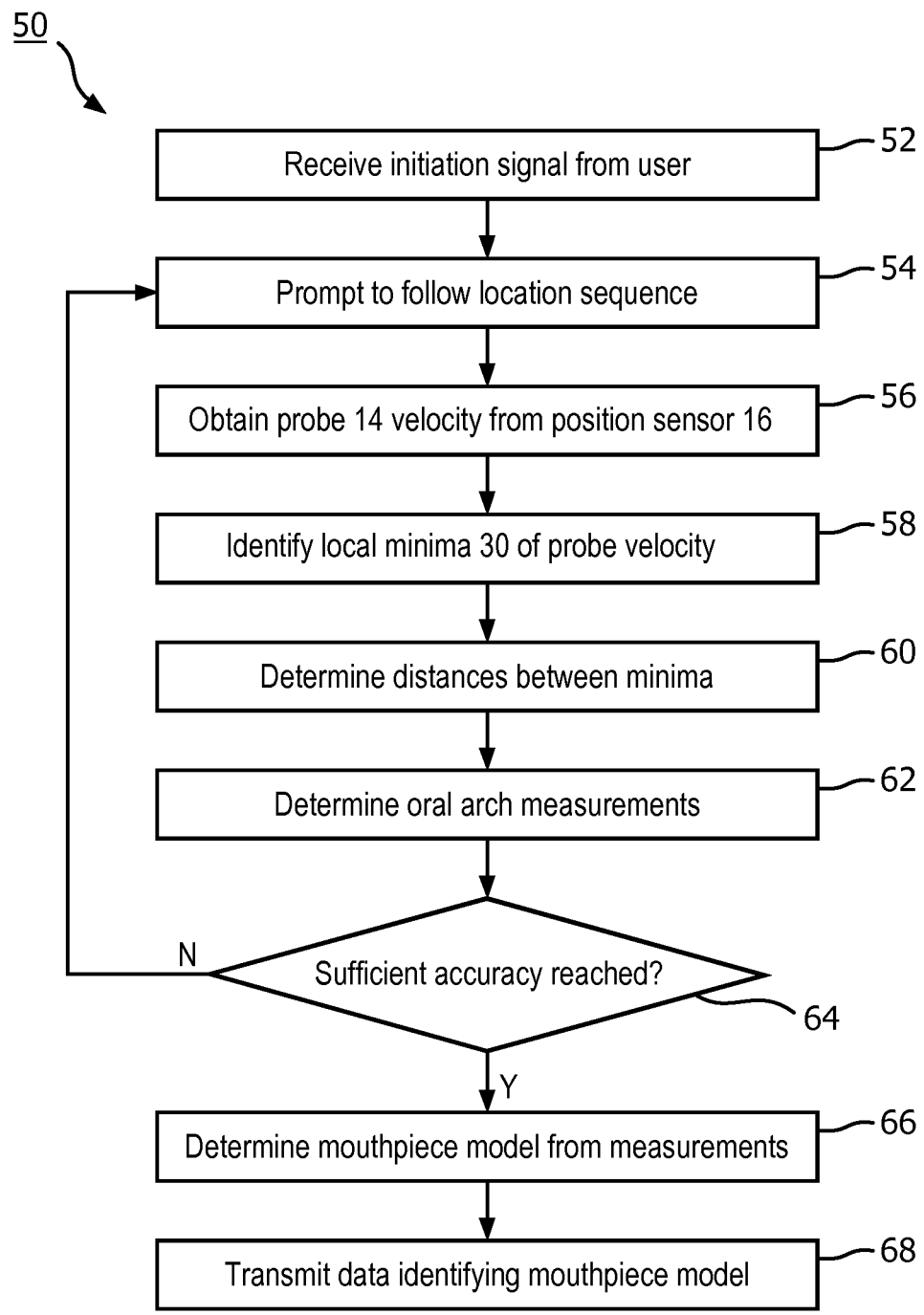
FIG. 6 is a flowchart illustrating a method for selecting a mouthpiece based on a user's measured oral arch geometry according to one embodiment disclosed herein.

In consideration of the above, FIG. 6 includes a flowchart that describes a method 50 according to one embodiment disclosed herein for utilizing a personal care system, such as the system 10, for enabling a user to obtain an appropriately sized mouthpiece. The method 50 begins at a step 52 at which the system receives a signal or other input from a user indicating that the user desires to initiate the measurement process. For example, the step 52 could be achieved by utilizing a remote device 26 (e.g., a smartphone) in communication with a personal care device (e.g., the personal care device 12) to initiate the measurement process. In other embodiments, the user may use buttons, a display, and/or other inputs on the personal care device itself to initiate contact. In one embodiment, the system is arranged to automatically detect that the user is following the instructed sequence with the tip or probe of the personal care device. For example, the controller 18 may be configured to receive the data from the position sensor 16 and identify that the pattern is being followed as it is expected that the position data that results from following the instructed sequence to be quantifiable distinguishable from normal brushing activity.

At a step 54, the user is instructed to follow the predetermined sequence as discussed above. For example, the instructed sequence could be communicated to the user via audio/visual signals from the personal care device, or a remote device such as a smart phone. The data from the position sensor(s) is collected as the user follows the instructed sequence by placing a tip or probe (e.g., the probe 14) of the personal care device at each instructed location. At a step 56, the system estimates the velocity from the position sensor data and at a step 58 the system identifies the local minima in the data. At a step 60, the distance between each location is determined by integrating the area between each adjacent pair of local minimums under the velocity curve generated in the step 56. For example, the steps 56, 58, and 60 may be achieved using the controller 18 as discussed above with respect to FIG. 5. As also discussed above with respect to FIG. 5, the step 60 may include performing a consistency check in which any data that includes values outside of expected ranges is flagged and/or deleted. If the consistency check fails, any or all of the steps 54, 56, 58, and/or 60 may be repeated. At a step 62, the system determines one or more oral arch measurements. For example, based on the position data collected by the position sensor 16, the controller 18 may be configured to determine oral arch widths such as the widths W1 or W2, and/or oral arch lengths such as the lengths L1 or L2 as discussed with respect to FIG. 4.

At a step 64 it is determined whether sufficient accuracy in the measurements has been achieved. For example, the measurements could be analyzed (e.g., by the controller 18) for significant variations between different cycles for the same or similar measurements. That is, the controller 18 in one embodiment may be arranged to identify whether any of the calculated distances (e.g., oral arch length) are outside of predetermined normal ranges for oral arches, whether any of the determined distances deviate significantly from the other determined distances, whether the user has followed the sequence a preset number of iterations, etc. In one embodiment, the controller 18 is configured to discard data that it identifies overly deviating from the other data points (e.g., using standard deviation or some other statistical metric). It is expected that a user should be able to move the probe 14 between any two points in their mouth in a relatively short amount of time, e.g., less than one second, so any transition between points that takes significantly longer than this (e.g., longer than 1.5 to 2 seconds) is discarded or not considered. If the measurements are determined to be inaccurate, the method 50 returns to the step 54, where the system can continue to instruct the user to place the tip or probe of the personal care device at instructed positions.

Once the measurements are identified as being sufficiently accurate at step 64, the method proceeds to step 66, at which the system selects a design for a mouthpiece (e.g., the mouthpiece 25) having a set of dimensions (e.g., the width W and the length L) that corresponds to the oral arch measurements (e.g., W1, W2, L1, L2) determined in the step 62. For example, the selected mouthpiece design may be selected from a predetermined set of possible mouthpieces. In this embodiment, each mouthpiece design could be designated with a different range of values for each of the measured oral arch dimensions (e.g., each mouthpiece having a different range of values corresponding to the dimensions W1, W2, L1, L2, etc.). In this way, the controller 18 can select or determine the appropriate mouthpiece design as the one having the combination of ranges that contain each of the oral arch measurements determined by the system 10. In one embodiment, the controller 18 custom generates a mouthpiece geometry based on the determined oral arch measurements.

At a step 68, information related to the selected mouthpiece is transmitted and/or provided to an intended recipient, such as the user, a healthcare provider for the user, or a mouthpiece supplier/manufacturer. In one embodiment, the step 68 includes providing the determined oral arch measurements and/or a model or part number for the selected mouthpiece, e.g., so that it can be bought or ordered by the user. In one embodiment, the step 68 includes initiating and/or completing a commercial transaction to purchase the selected mouthpiece, or providing the user with an internet address at which the selected mouthpiece can be ordered. In one embodiment, the step 68 includes transmitting data related to a computer or CAD model of the mouthpiece, such that the mouthpiece can be made by a three-dimensional printer. The step 68 may be implemented using the device 12, or a remote device 26 such as a smartphone or other computing device.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. As used herein in the specification and in the claims, "or" should be understood to have the same meaning as "and/or" as defined above.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A method for selecting a design for a mouthpiece for a user, comprising:
    receiving a signal with a personal care system to initiate oral arch measurements using a personal care device,
    collecting data from a position sensor related to a location of a probe of the personal care device as the probe is moved about an oral arch of the user;
    determining, by a controller of the personal care system, a dimension (W1, W2, L1, L2) of the oral arch from the data;
    selecting, by the controller, a design for a mouthpiece for the user based on the dimension of the oral arch; and
    transmitting information identifying the mouthpiece design to an intended recipient.

2. The method of claim 1, further comprising transmitting a sequence of a plurality of oral arch positions at which the user is instructed to touch the probe of the personal care device.

3. The method of claim 2, wherein the positions in the sequence include at rear molars, at front teeth, at canines, or a combination including at least one of the foregoing.

4. The method of claim 2, wherein at least a portion of the sequence is repeated or reversed in order and then repeated.

5. The method of claim 2, wherein the determining includes:
    obtaining a velocity of the probe from the data;
    generating a velocity curve as the velocity over time;
    identifying a plurality of local minimums in the velocity curve;
    integrating an area under the velocity curve and between an adjacent pair of local minimums; and determining the dimension of the oral arch as a result of the integrating.

6. The method of claim 5, further comprising correlating each of the positons to one of the local minimums using a known order of the sequence.

7. The method of claim 5, further comprising connecting a line between the adjacent pair of local minimums, and bounding the area with the line to eliminate drift or sensor error during the integrating.

8. The method of claim 5, wherein the data includes acceleration data and the obtaining includes integrating the acceleration data.

9. The method of claim 1, wherein the position sensor includes a plurality of position sensors and the collecting includes collecting data with each of the positions sensors.

10. The method of claim 9, wherein the plurality of position sensors includes a camera or proximity sensor and an inertial measurement unit.

11. The method of claim 1, wherein the controller is included by the personal care device, a remote device separate from the personal care device, or a combination including at least one of the foregoing.

12. The method of claim 11, wherein the remote device is a charging station, smartphone, or other computing device in communication with the position sensor.

13. A personal care system comprising:
    a personal care device having a probe;
    a position sensor configured to collect data related a position of the probe; and
    a controller configured to:
        determine a dimension (W1, W2, L1, L2) of an oral arch of a user from the data;
        select a design for a mouthpiece for the user based on the dimension of the oral arch;
        and transmit information identifying the mouthpiece design to an intended recipient.

14. The personal care system of claim 13, wherein the personal care device is an electric toothbrush, an interdental cleaning device, a flossing device, or an oral irrigator.

15. The personal care system of claim 13, further comprising a remote device in communication with the position sensor, the remote device comprising the controller.

* * * * *